US012129489B2

(12) United States Patent
Seo et al.

(10) Patent No.: US 12,129,489 B2
(45) Date of Patent: Oct. 29, 2024

(54) YARN FOR CELL CULTURE SCAFFOLD, PLY YARN COMPRISING SAME AND FABRIC COMPRISING THE SAME

(71) Applicant: AMOGREENTECH CO., LTD., Gimpo-si (KR)

(72) Inventors: In Yong Seo, Seoul (KR); Seon Ho Jang, Seoul (KR); Song Hee Koo, Gyeonggi-do (KR); Chan Kim, Gwangju (KR); Seoung Hoon Lee, Gyeonggi-do (KR)

(73) Assignee: AMOGREENTECH CO., LTD., Gimpso-si (KR)

( * ) Notice: Subject to any disclaimer, the term of this patent is extended or adjusted under 35 U.S.C. 154(b) by 1127 days.

(21) Appl. No.: 16/304,015

(22) PCT Filed: May 24, 2017

(86) PCT No.: PCT/KR2017/005426
§ 371 (c)(1),
(2) Date: Nov. 21, 2018

(87) PCT Pub. No.: WO2017/204564
PCT Pub. Date: Nov. 30, 2017

(65) Prior Publication Data

US 2019/0203178 A1 Jul. 4, 2019

(30) Foreign Application Priority Data

May 25, 2016 (KR) ........................ 10-2016-0063854

(51) Int. Cl.
*D02G 3/02* (2006.01)
*A61L 27/16* (2006.01)
(Continued)

(52) U.S. Cl.
CPC ............ *C12N 5/0656* (2013.01); *A61L 27/16* (2013.01); *A61L 27/38* (2013.01); *A61L 27/3834* (2013.01);
(Continued)

(58) Field of Classification Search
None
See application file for complete search history.

(56) References Cited

U.S. PATENT DOCUMENTS 8,226,715 B2 7/2012 Hwang
8,926,933 B2 1/2015 Zhang
(Continued)

FOREIGN PATENT DOCUMENTS

CN 101437663 A 5/2009
JP 2005-226210 A 8/2005
(Continued)

OTHER PUBLICATIONS

Freeman et al., Journal of Biomechanics 40 (2007) 2029-2036 (Year: 2007).*
(Continued)

*Primary Examiner* — Evelyn Y Pyla
(74) *Attorney, Agent, or Firm* — ROTHWELL, FIGG, ERNST & MANBECK, P.C.

(57) ABSTRACT

A yarn including a plurality of twists formed by twisting single fiber strand or multiple fiber strands; and fiber grooves, which are spaces formed between the twists, to provide three-dimensional growth spaces and migration paths for cells. Accordingly, a cell proliferation rate and cell viability may be enhanced by creating microenvironments suitable for migration, proliferation and differentiation of cultured cells. In addition, cell clusters having more uniform shapes may be easily implemented by forming the proliferation spaces and migration paths for the cultured cells as
(Continued)

similar as possible to each other in each scaffold. Further, the cells cultured thereby can be cultured in a suitable shape and structure to be applied to an in vitro experimental model or transplanted into the body of an animal, and can be widely applied in various products used in a cell culture or tissue engineering field.

6 Claims, 10 Drawing Sheets

Specification includes a Sequence Listing.

(51) Int. Cl.

| | |
|---|---|
| ***A61L 27/38*** | (2006.01) |
| ***A61L 27/44*** | (2006.01) |
| ***C12N 5/00*** | (2006.01) |
| ***C12N 5/077*** | (2010.01) |
| ***D02G 1/02*** | (2006.01) |
| ***D02G 3/26*** | (2006.01) |
| ***D02G 3/44*** | (2006.01) |
| ***D03D 15/00*** | (2021.01) |

(52) U.S. Cl.

CPC ................ *A61L 27/44* (2013.01); *C12N 5/00* (2013.01); *D02G 1/02* (2013.01); *D02G 1/0206* (2013.01); *D02G 1/0286* (2013.01); *D02G 1/0293* (2013.01); *D02G 3/02* (2013.01); *D02G 3/26* (2013.01); *D02G 3/448* (2013.01); *D03D 15/00* (2013.01); *C12N 2533/30* (2013.01); *D10B 2201/02* (2013.01); *D10B 2321/042* (2013.01); *D10B 2331/02* (2013.01); *D10B 2331/04* (2013.01); *D10B 2509/00* (2013.01)

(56) References Cited

U.S. PATENT DOCUMENTS

2012/0078297 A1* 3/2012 Chun .................... A61L 17/005 57/295
2014/0005797 A1* 1/2014 Park ........................ A61L 27/54 623/23.72
2015/0056256 A1* 2/2015 Essaidi .................. D06M 11/51 87/8
2017/0273775 A1* 9/2017 Rocco ..................... A61L 27/58

FOREIGN PATENT DOCUMENTS

| | | | | | |
|---|---|---|---|---|---|
| JP | 2011-147790 | A | | 8/2011 | |
| JP | 2011194270 | A | | 10/2011 | |
| KR | 10-2008-0104932 | A | | 12/2008 | |
| KR | 10-1075882 | | * | 10/2011 | ............... D02G 3/22 |
| KR | 10-1075882 | B1 | | 10/2011 | |
| KR | 101104305 | B1 | | 1/2012 | |
| KR | 10-1198196 | B1 | | 11/2012 | |
| KR | 1020150116941 | A | | 10/2015 | |

OTHER PUBLICATIONS

Understanding Basis Weight, Quill.com, retrieved from the internet Apr. 21, 2022: https://www.quill.com/content/index/xerox-paper/pdfs/Quill-UnderstandingBasisWtFlyer.pdf (Year: 2022).*
Grammage—What does grammage mean?, LabelPlanet, retrieved from the internet Apr. 21, 2022: https://www.labelplanet.co.uk/glossary/grammage/#:~:text=Definition%20of%20GRAMMAGE%3A&text=The%20grammage%20of%20a%20material,is%20a%20commonly%20used%20alternative. (Year: 2022).*
Zhou et al., J. Mater. Res., vol. 27, No. 3, Feb. 14, 2012, pp. 537-544 (Year: 2012).*
Kim et al., Tissue Engineering, vol. 12, No. 2, 2006, pp. 221-233 (Year: 2006).*
Horan et al., Journal of Biomechanics 39 (2006) 2232-2240 (Year: 2006).*
He et al., Fibers and Polymers 2013, vol. 14, No. 11, 1857-1863 (Year: 2013).*
Mooneghi et al., Polymer Engineering and Science—2015, pp. 1805-1811 (Year: 2015).*
Kim et al., KR10-1075882, English machine translation (Year: 2011).*
International Search Report cited in PCT/KR2017/005426 dated Aug. 28, 2017, 3 pages.

* cited by examiner

YARN FOR CELL CULTURE SCAFFOLD, PLY YARN COMPRISING SAME AND FABRIC COMPRISING THE SAME

CROSS REFERENCE TO RELATED APPLICATION

This application is a 35 U.S.C. 371 National Phase Entry Application from PCT/KR2017/005426, filed May 24, 2017, which claims the benefit of Korean Patent Application No. 10-2016-0063854 filed on May 25, 2016, the disclosures of which are incorporated herein in their entirety by reference.

SEQUENCE LISTING

The present application includes a Sequence Listing filed in electronic format. The Sequence Listing is entitled "SOP114369US.ST25.txt" created on Nov. 21, 2018, and is 12,000 bytes in size. The information in the electronic format of the Sequence Listing is part of the present application and is incorporated herein by reference in its entirety.

TECHNICAL FIELD

The present invention relates to yarn for a cell culture scaffold, and more particularly, to yarn for a cell culture scaffold which improves cell viability by creating microenvironments suitable for adhesion, migration, proliferation and differentiation of cultured cells, allows cells to be three-dimensionally proliferated and allows a cell cluster to be easily proliferated in a uniform shape to express physical, chemical and biological properties similar to a body structure, ply yarn having the same, and a fabric having the same.

BACKGROUND ART

Recently, according to expansion of the use of cultured cells in disease treatment, interest in and research on cell culture are increasing. Cell culture is a technique for collecting cells from a living organism and culturing the cells outside the living organism, and the cultured cells may be used in treatment of various diseases through differentiation into various types of tissue of a body, for example, the skin, organs, nerves, etc. to be grafted into the body, or grafting in an undifferentiated state to attain engraftment and differentiation at the same time.

One of the development challenges to be solved in cell culture is the component material, structure and morphology of a scaffold capable of culturing and differentiating cells and being grafted to tissue along with cells. However, cells cultured using a previously-developed scaffold for cell culture were not cultured in a three-dimensional structure similar to a body and had low viability, and therefore were not suitable for use as an in vitro experiment model or cells for grafting.

In addition, even when cells are three-dimensionally proliferated, the shape of a proliferated cell cluster varies according to the shape, morphology and structure of a scaffold proliferating the cells, and in this case, a reaction of the cell cluster may vary according to a physical or chemical stimulus applied to the cell cluster. Particularly, if there are different responses exhibited by cultured cell clusters, uniform and reproducible outcomes cannot be obtained, and therefore it is not suitable for use in testing or experimentation of the proliferated cell cluster.

In Korean Patent No. 10-1104305 (Patent Literature 1), a method of producing a Janus-shaped polymer microfiber for tissue engineering, which has a porous surface, is disclosed.

In Patent Literature 1, a polyurethane microfiber produced by continuously injecting both of a photopolymerizable polyurethane monomer and a continuous-phase aqueous solution which is not mixed with the monomer into a microflow to form a monomer jet stream and applying UV rays to discharge a photocured monomer to the continuous phase is applied as a scaffold for tissue engineering is disclosed. Since the thickness of the produced fiber is several hundred micrometers, the size, structure and arrangement of pores are not uniform, due to large pores, initial cell adhesion is actively performed, and although cells are adhered, there may have problems in culture, for example, migration, proliferation, growth, etc.

In addition, Korean Unexamined Patent Application No. 10-2015-0116941 (Patent Literature 2) discloses a hydrophilic nanofiber cell scaffold which includes a PVP-b-PCL block copolymer. In Patent Literature 2, a cell scaffold formed of a nanofiber of a biocompatible polymeric material to have a hydrophilic structure is favorable for initial cell adhesion. However, due to the characteristic of electrospinning, the nanofiber is randomly arranged, it is difficult to form a pore with a size of 1 μm or more, there is a limitation to growth, proliferation, migration and differentiation after cell adhesion, and there is a concern that it may not have an appropriate effect in application as a scaffold of cells with a specific shape.

Therefore, it is necessary to create a scaffold environment similar to a body structure so that cells can be three-dimensionally cultured and proliferated with a structure similar to the body, and cultured to have a cell cluster with uniform morphology.

DISCLOSURE

Technical Problem

The present invention is devised by taking the above-mentioned problems into account, and thus directed to providing yarn and a fabric for a cell culture scaffold which improves cell proliferation rate and cell viability by creating microenvironments suitable for migration, proliferation and differentiation of cultured cells.

In addition, the present invention is also directed to providing yarn and a fabric for a cell culture scaffold which facilitates a cell cluster to be produced to have a more uniform shape by forming the proliferation spaces and migration paths for the cultured cells as similar as possible to each other in each scaffold.

In addition, the present invention is also directed to providing yarn and a fabric for cell culture which can culture cells to have a shape or structure similar to the actual animal body such that the cells can be suitable for being applied to grafting into an in vitro experimental model or animal.

In addition, the present invention is also directed to providing ply yarn and a fabric for a cell culture scaffold which can be widely applied in various types of products used in a cell culture or tissue engineering field, including a bioreactor, a cell culture container, an implantable kit, etc., using the yarn according to the present invention.

Technical Solution

To solve the above-described problems, the present invention provides yarn for a cell culture scaffold, which includes a plurality of twists formed by twisting single or multiple fiber strands; and fiber grooves, which are spaces formed between the twists, to provide three-dimensional growth spaces and migration paths for cells.

According to an exemplary embodiment of the present invention, the fiber may be spun yarn, filament yarn or slitting yarn.

In addition, the fiber may include, as a fiber-forming component, any one or more non-biodegradable components selected from the group consisting of polystyrene (PS), polyethylene terephthalate (PET), polyethersulfone (PES), polyvinylidene fluoride (PVDF), polyacrylonitrile (PAN), polydimethylsiloxane (PDMS), a polyamide, a polyalkylene, a poly(alkylene oxide), a poly(amino acid), a poly (allylamine), polyphosphazene and a polyethyleneoxide-polypropyleneoxide block copolymer, or any one or more biodegradable components selected from the group consisting of polycaprolactone, polydioxanone, polyglycolic acid, poly(L-lactide) (PLLA), poly(DL-lactide-co-glycolide) (PLGA), polylactic acid and polyvinyl alcohol.

In addition, the yarn may have a twist number of 100 to 5000 twists/meter T/m and a twist angle of 20 to 60°.

In addition, the yarn may have a fineness of 0.1 to 300 deniers.

In addition, the fiber constituting the yarn may have a fineness of 0.01 to 30 deniers.

In addition, the yarn may include multiple fiber strands, and further include microfiber grooves, which are spaces between the microfilaments, on the outer surface of the yarn.

In addition, the slitting yarn may be a nanofiber web with a three-dimensional network structure cut to have a predetermined width. Here, the nanofiber web may have a basis weight of 0.1 to 100 $g/m^2$, and a width of 0.1 to 30 mm.

In addition, the fiber may further include a physiologically active component inducing any one or more of adhesion, migration, growth, proliferation and differentiation of cells on the outer surface of the microfilament.

The physiologically active component may include any one or more among any one or more compounds selected from the group consisting of a monoamine, an amino acid, a peptide, a saccharide, a lipid, a protein, a glucoprotein, a glucolipid, a proteoglycan, a mucopolysaccharide and a nucleic acid, and a cell.

The present invention also provides ply yarn for a cell culture scaffold, which includes a plurality of the yarns according to the present invention.

The present invention also provides ply yarn for a cell culture scaffold, which includes a plurality of macrotwists formed by twisting the yarn according to the present invention, and macrofiber grooves, which are spaces between the macrotwists, providing three-dimensional growth spaces and migration paths for cells.

In addition, the ply yarn may have a fineness of 0.5 to 1000 deniers, a twist number of 100 to 5000 T/m, and a twist angle of 20 to 60°.

The present invention also provides a fabric for a cell culture scaffold, which includes the yarn according to the present invention.

The present invention also provides a fabric for a cell culture scaffold which includes the ply yarn according to the present invention.

The present invention also provides a graft for tissue engineering, which includes the fabric according to the present invention; and cells cultured along fiber grooves of yarn for a cell culture scaffold in the fabric.

In addition, the yarn for a cell culture scaffold, double yarn for a cell culture scaffold, combination yarn for a cell culture scaffold, fabric for a cell culture scaffold which includes any one or more thereof, and graft for tissue engineering according to the present invention may be suitable for culturing and/or grafting cells including any one or more types of stem cells selected from the group consisting of totipotent stem cells, pluripotent stem cells, multipotent stem cells, oligopotent stem cells and single stem cells, and one or more types of differentiated cells selected from the group consisting of hematopoietic stem cells, liver cells, fiber cells, epithelial cells, mesothelial cells, endothelial cells, muscle cells, nerve cells, immune cells, adipose cells, cartilage cells, bone cells, blood cells and skin cells.

Hereinafter, terms used herein will be described.

The term "extracellular matrix (ECM)" used herein is a substrate which surrounds the outside of a cell, occupies a space between cells, and has a network structure usually consisting of proteins and polysaccharides.

The "motif" used herein is a peptide comprising an amino acid sequence, which can structurally/functionally interact with a receptor included in a protein, a glucoprotein, etc. in the ECM playing a critical role in cell adhesion, migration, differentiation, etc. to pass through a surface of a cell membrane or a membrane, and is isolated from a cell or artificially produced using a gene cloning technique.

The term "three-dimensional cell cluster" used herein refers to a group of cells which are three-dimensionally collected.

The term "ply yarn" used herein is a yarn assembly formed by combining and twisting two or more strands of yarn, and there is no limitation to the origin of each kind of yarn for plying from spun yarn or filament yarn. In addition, combination yarn formed by twisting different types of yarns is also included in the ply yarn.

Advantageous Effects

According to the present invention, a cell proliferation rate and cell viability can be improved by creating microenvironments suitable for adhesion, transmission, proliferation and differentiation of cultured cells. In addition, a cell cluster with a more uniform shape can be easily realized by forming scaffolds to have proliferation spaces and migration paths for cells as similar as possible to each other in each scaffold. Further, the cells cultured thereby can be cultured in a suitable shape and structure to be applied to an in vitro experimental model or transplanted into the body of an animal, and can be widely applied in various products used in a cell culture or tissue engineering field, for example, a bioreactor, a cell culture container, a kit for grafting into a body, etc.

DESCRIPTION OF DRAWINGS

FIGS. 3A and 3B show examples of slitting yarn included in an exemplary embodiment of the present invention, in which FIG. 3A is an enlargement of a nanofiber web before slitting yarn is produced, and FIG. 3B is an enlargement of a nanofiber web after slitting yarn is produced.

FIGS. 7A-C show a set of images of an intermediate step for producing slitting yarn according to an exemplary embodiment of the present invention, in which FIG. 7A is an image of slitting yarn produced by first slitting to a width of 50 mm, FIG. 7B is an image illustrating a process of precisely slitting the yarn obtained through the first slitting to a width of 1.5 mm, and FIG. 7C is an image illustrating a process of winding the slitting yarn with a width of 1.5 mm, produced as described in FIG. 7B.

MODES OF THE INVENTION

Figure 1:
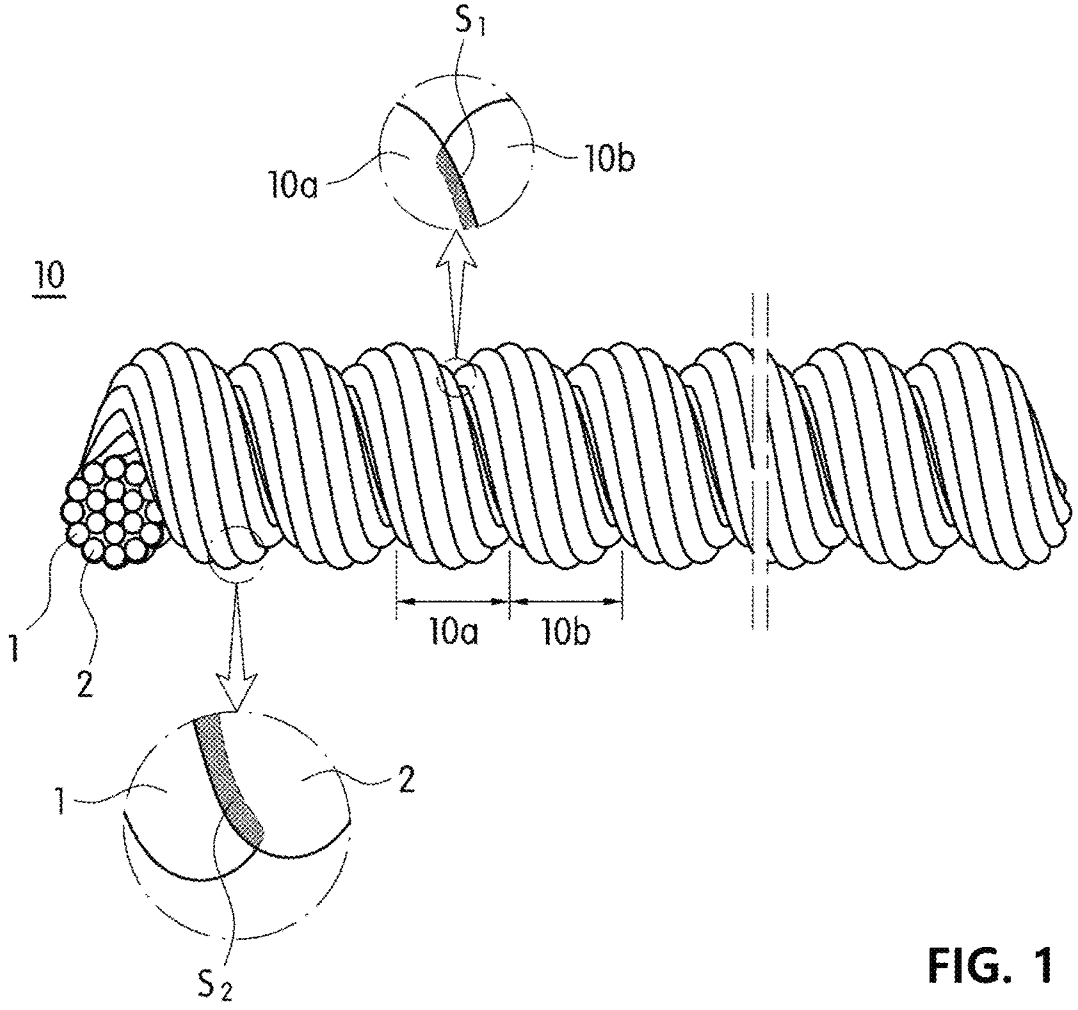
FIG. 1 is a perspective view and a partial enlargement of yarn according to an exemplary embodiment of the present invention.

Hereinafter, embodiments of the present invention will be described in detail with reference to the accompanying drawings so that those of ordinary skill in the art can easily carry out the present invention. The present invention may be implemented in a variety of different forms, and is not limited to the embodiments described herein. For clear explanation of the present invention in the drawings, parts that are not related to the description are omitted, and the same numerals denote the same or like components throughout the specification.

As shown in FIG. 1, yarn for a cell culture scaffold 10 according to an exemplary embodiment of the present invention includes a plurality of twists 10*a* and 10*b* formed by twisting multiple fiber strands 1 and 2, and fiber grooves S1, which are spaces formed between the twists 10*a* and 10*b* on the outer surface of the yarn 10 to provide three-dimensional growth spaces and migration paths for cells. In addition, the yarn may be formed by twisting one fiber strand, which is different from FIG. 1.

Describing the fiber grooves S1 in detail, as shown in FIG. 1, when a bundle of multiple fiber strands 1 and 2 is fixed, and the fiber bundle is continuously twisted in one direction, a plurality of twists are continuously formed by false-twisting the fiber bundle from a fixed end to the other end, due to a curvature of the fiber bundle itself, fiber grooves S1, which are V- or U-shaped spaces formed between twists, are formed. The fiber grooves S1 are formed on the outer surface of the yarn in a spiral shape along the direction of twisting the fiber bundle. If the yarn is fixed at a predetermined and subjected to uniform twisting, patterns, for example, a height of the fiber grooves S1 formed on the outer surface of the yarn and a pitch interval of the spirally-continuous fiber grooves may be uniform.

Meanwhile, when cells are cultured in a yarn-state scaffold, the cells may be cultured over several yarns, or if the yarn has a high fineness, may be cultured while being adhered to the outer surface of the yarn. The cells cultured over several yarns are difficult to stably adhere due to the flow of the yarns, and in this case, since the cells cultured in the scaffold are easily detached, it is very difficult to culture cells in a three-dimensional cluster. In addition, even when cells are cultured by being adhered to the outer surface of the yarn having a high fineness, the cells may be only two-dimensionally adhered to the outer surface of the yarn, and thus may be easily detached. In addition, when cells are cultured over several yarns or cultured on the outer surface of single yarn, cluster forms of the cultured cells are not uniform.

However, in consideration of a size of the cultured cells, as described above, when fiber grooves are formed with uniform pitch intervals and heights, the culture cells are settled in approximately V- or U-shaped fiber grooves to be three-dimensionally bonded on the outer surface of the yarn. Therefore, the fiber grooves are suitable for stable culture of cells, prevention of the detachment of the cultured cells, and three-dimensional culture of the cells. In addition, since the twisted yarn is increased in strength of the yarn and easily maintains a shape, there is an advantage in that cells can be supported more stably in a liquid culture medium or a flowing culture medium. Further, as the fiber grooves formed in the twisted yarn are formed continuously in the longitudinal direction of the yarn, there is an advantage in that the cultured cells can be more stably migrated, proliferated and differentiated along the scaffold. Particularly, the migration path provided by the fiber grooves may reduce resistance during cell migration such that the cells can be more easily migrated. Moreover, a shape of the cell cluster proliferated through migration may be dependent on a form of the fiber grooves, and as described above, due to the uniform patterns such as the form and twists of the fiber grooves, there is an advantage in that the shape of the proliferated cell cluster can also be formed to be very uniform due to stimulation to cells in a uniform orientation. In addition, the cell clusters that are collectively cultured to have arrangeability according to the patterns of the fiber grooves may facilitate a series of activities including a cell signaling mechanism to be observed and may be advantageous for confirmation of reactivity.

A degree of false-twisting the yarn may be determined by considering a type and a size of cells to be cultured and a shape and a size of a cell cluster. As an example, the yarn may have a twist number of 100 to 5000 T/m and a twist angle of 20 to 60°. If the twist number is less than 100 T/m, the yarn may be shook a lot due to an external force caused by a flowing culture medium, and when the yarn includes multiple fiber strands, it may be difficult to stably culture cells due to additional shaking caused by a distance between the fibers. In addition, if the twist number is more than 5000 T/m, due to the fibers or abrasion between the fibers, the strength of the yarn may be more decreased, and therefore, a frequency of yarn breakage may be considerably increased. In addition, due to excessive twisting, the twists are closer to each other, and therefore a volume of the fiber grooves may be reduced.

Figure 2:
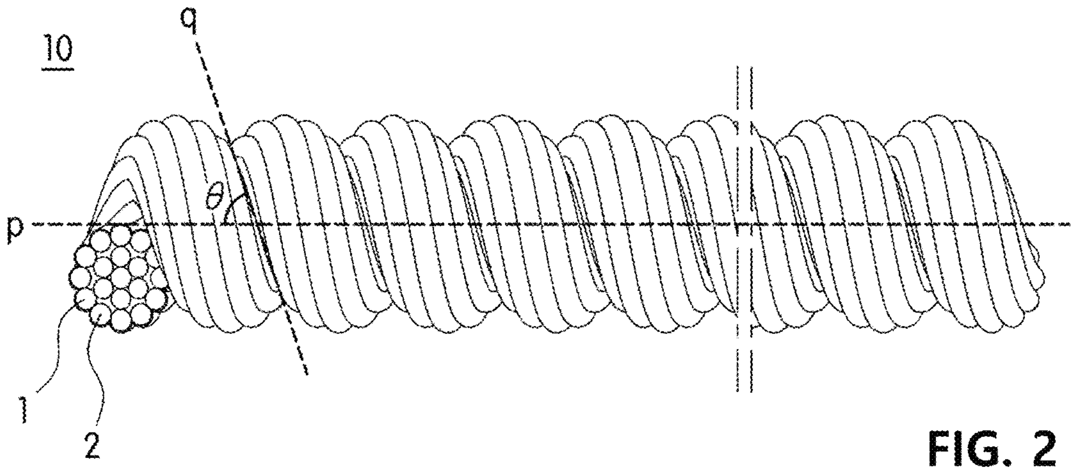
FIG. 2 is a perspective view of yarn according to an exemplary embodiment of the present invention.

In addition, the yarn may have a twist angle of 20 to 60°. As shown in FIG. 2, the twist angle refers to an acute angle(°) between a yarn axis (p) and a twist (q) on the surface of the yarn. If the acute angle(°) is less than 20°, due to less twisting of the yarn, it is difficult to form fiber grooves, and when the yarn consists of several fiber strands, the cells may be cultured over several strands of fiber, and thus the stability may be reduced. In addition, to form fiber grooves with a low twist number, twisting should be performed while a high tension is applied to the yarn, and in this case, the yarn may be broken. Therefore, it is difficult to produce the yarn, and productivity may be considerably reduced.

The fineness of the yarn may be determined by considering a type and a size of cells to be cultured, and may be preferably 0.1 to 300 deniers. If the fineness is less than 0.1 deniers, due to a decrease in specific surface area to which cells are adhered, it can be difficult to produce a cell cluster to a desired level, and due to a low mechanical strength, it may be difficult to stably culture cells. In addition, when the fineness is more than 300 deniers, due to an excessive diameter of the scaffold, a volume or depth of the U- or V-shaped groove formed by twisting may be greater, and in this case, loaded cells may be grown intermittently by forming clusters in the fiber grooves, rather than being migrated, and it may be difficult to obtain a cell cluster having uniform size and shape.

In addition, the yarn may consist of single or multiple fiber strands, and the number of microfilaments included in the yarn may be suitably changed by considering the fineness of the yarn and the volume of the fiber grooves S1, which are determined to suit the type and size of cells to be cultured and the shape and size of a cell cluster, and thus the present invention is not particularly limited thereto.

However, when a single fiber strand is twisted, the fiber groove may be present between the twists, but when several fiber strands are twisted, more microfiber grooves may be formed also in spaces between the fibers, and may further provide cell culture spaces and/or cell migration paths. Specifically, as shown in FIG. 1, due to the curvature of the outer surface, a microfiber groove S2 may be further included between a first fiber 1 and a second fiber 2, and may serve as an additional culture space or migration path of cells. In other words, in cell culture, cells may not be settled in an approximately V- or U-shaped space of each fiber groove S1, some cells may be settled on the outer surface of the yarn, other than that space, and due to the microfiber grooves S2, cells may be stably adhered and smoothly migrated.

The single or multiple fibers included in the yarn may be spun yarn, filament yarn or slitting yarn.

When the fiber is spun yarn or filament yarn, the fineness may be 0.01 to 30 deniers. However, the present invention is not limited thereto, and the fineness may be changed to be suitable for the type and size of cells to be cultured and the shape and size of a cell cluster.

In addition, the spun yarn may be produced from raw cotton by a known method. In addition, the filament yarn may be produced by spinning according to a known method, and the spinning may be performed by a known spinning method such as chemical spinning or electrospinning.

Figure 3A:
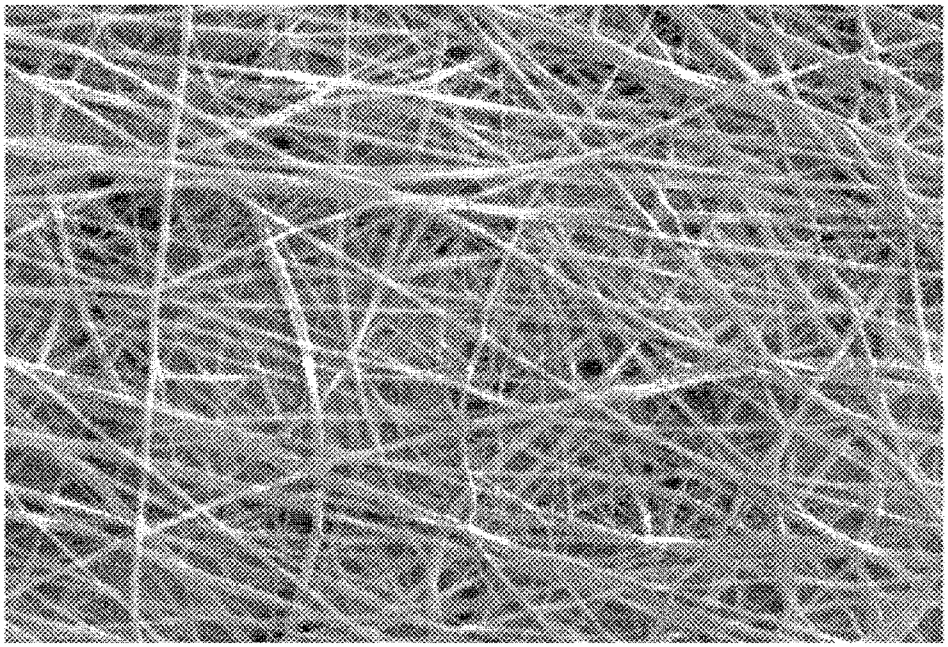
Figure 3B:
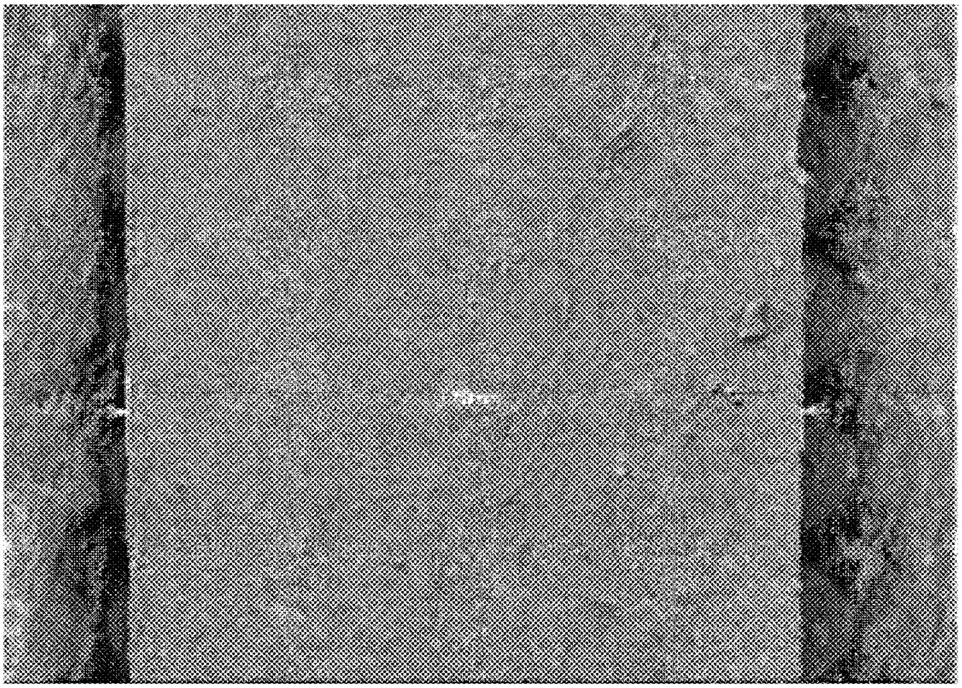

In addition, the slitting yarn may be produced by cutting a sheet-type fiber assembly or a fabric to have a predetermined width. Preferably, the slitting yarn may be fibers produced by cutting a sheet-type nanofiber web having a three-dimensional network structure to have a predetermined width. Here, the nanofiber web may be compressed with a constant pressure to improve the ease of a slitting process, and increase the strength of the slitting yarn. For example, FIG. 3A shows a sheet-type nanofiber web having a three-dimensional network structure, which may be compressed and cut to a predetermined width, thereby producing slitting yarn as shown in FIG. 3B.

The slitting yarn may be a fiber produced by cutting a fiber web having a basis weight of 0.1 to 100 g/m$^2$, preferably, 0.1 to 50 g/m$^2$, and more preferably, 0.1 to 20 g/m$^2$ to have a width of 0.1 to 30 mm. If the nanofiber web is slit to have a width of less than 0.1 mm, there are problems in which the slitting yarn may not be easily cut, but easily trimmed due to a tension and a torque applied during false twisting. In addition, when the fiber web is slit to have a width of more than 30 mm, an irregular twist may be formed during twisting.

Figure 4:
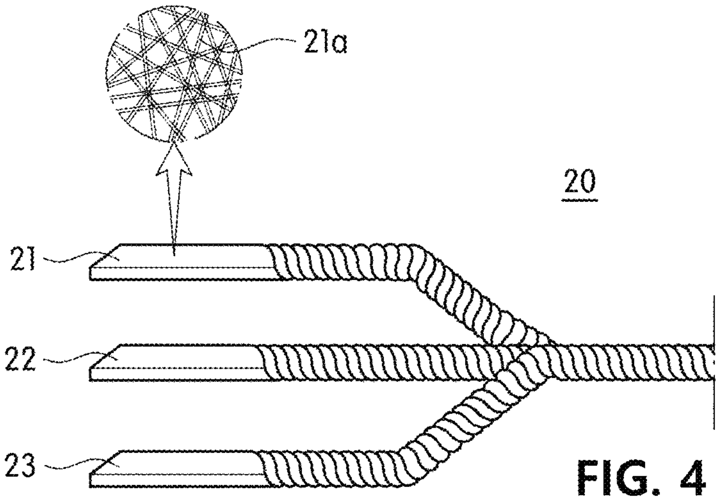
FIG. 4 is an exploded perspective view of yarn according to an exemplary embodiment of the present invention, which is produced by twisting a fiber around slitting yarn.

In addition, as shown in FIG. 4, yarn 20 including a plurality of twists and fiber grooves may be produced by braiding and twisting first slitting yarn 21, second slitting yarn 22 and third slitting yarn 23. Here, the slitting yarns 21, 22 and 23 may be nanofiber webs having a three-dimensional network structure, formed of a plurality of fibers 21*a*, preferably, nanofibers. Due to a microfiber such as the nanofiber constituting the nanofiber web, the yarn may be more tightly adhered to the cells. In addition, when the size of the cells to be cultured is small, a fine space in the fiber web may provide another culture space in which cells will be cultured. Moreover, since a cell culture solution can pass through the fiber web, the yarn produced by twisting the fiber webs also has permeability to the cell culture solution, and therefore there is an advantage of culturing cells more stably and with high efficiency.

The above-described fibers may be formed of a known fiber-forming component to be formed in the form of a fiber, and may be produced by selecting a suitable material depending on the type of a fiber. Since a material may vary depending on a specific purpose, for example, requirement of a decomposition property, the present invention is not particularly limited thereto. The fiber-forming component may include a cellulose component such as cotton or hemp, a protein component such as wool or silk, or a natural fiber component such as a mineral component. In addition, the fiber-forming component may be a known artificial fiber component.

Meanwhile, the fiber-forming component may include any one or more non-biodegradable components selected from the group consisting of polystyrene (PS), polyethylene terephthalate (PET), polyethersulfone (PES), polyvinylidene fluoride (PVDF), polyacrylonitrile (PAN), polydimethylsiloxane (PDMS), a polyamide, a polyalkylene, a poly(alkylene oxide), a poly(amino acid), a poly(allylamine), polyphosphazene and a polyethyleneoxide-polypropyleneoxide block copolymer, or any one or more biodegradable components selected from the group consisting of polycaprolactone, polydioxanone, polyglycolic acid, poly (L-lactide) (PLLA), poly(DL-lactide-co-glycolide) (PLGA), polylactic acid and polyvinyl alcohol depending on purpose.

In addition, the above-described fibers may further include a functional material, in addition to the fiber-forming component. As an example of the functional material, the fiber may further include a physiologically active component inducing any one or more of cell adhesion, migration, growth, proliferation and differentiation. The physiologically active component may include any one or more among any one or more compounds selected from the group consisting of a monoamine, an amino acid, a peptide, a saccharide, a lipid, a protein, a glucoprotein, a glucolipid, a proteoglycan, a mucopolysaccharide and a nucleic acid, and a cell. The materials may be, specifically, present in the ECM.

Meanwhile, the physiologically active component may include a motif. The motif may be a natural or recombinant peptide comprising a predetermined amino acid sequence included in any one or more selected from proteins, glucoproteins and proteoglycans included in a growth factor or the ECM. Specifically, the motif may include a predetermined amino acid sequence included in any one or more growth factors (GFs) selected from the group consisting of adrenomedullin, angiopoietin, a bone morphogenetic protein (BMP), a brain-derived neurotrophic factor (BDNF), an epithelial growth factor (EGF), erythropoietin, a fibroblast growth factor, a glial cell line-derived neurotrophic factor (GDNF), a granulocyte colony-stimulating factor (G-CSF), a granulocyte macrophage colony-stimulating factor (GM-CSF), growth differentiation factor-9 (GDF9), a hepatocytic growth factor (HGF), a hepatoma-derived growth factor (HDGF), an insulin-like growth factor (IGF), a keratinocyte growth factor (KGF), a migration-stimulating factor (MSF), myostatin (GDF-8), a nerve growth factor (NGF), a platelet-derived growth factor (PDGF), thrombopoietin (TPO), a T-cell growth factor (TCGF), neuropilin, transforming growth factor-α (TGF-α), transforming growth factor-β (TGF-β), tumor necrosis factor-α (TNF-α), a vascular endothelial growth factor (VEGF), IL-1, IL-2, IL-3, IL-4, IL-5, IL-6 and IL-7. Alternatively, the motif may include a predetermined amino acid sequence included in any one or more selected from the group consisting of hyaluronic acid, heparin sulfate, chondroitin sulfate, dermatan sulfate, keratan sulfate, alginate, fibrin, fibrinogen, collagen, elastin, fibronectin, bitronectin, carderine and laminin in the ECM. In addition, the motif may include both of a predetermined amino acid sequence included in the growth factor and a predetermined amino acid sequence included in the ECM. More preferably, the motif may include one or more selected from the group consisting of proteins comprising amino acid sequences of SEQ. ID. NOs: 8 to 28 and one or more selected from the group consisting of proteins in which at least two of the proteins are fused, but the present invention is not limited thereto.

Meanwhile, the motif may be integrated with the above-described adhesive component by a covalent bond. For example, when the adhesive component is a protein, the motif may be covalently bonded to the N-terminus and/or the C-terminus of a polypeptide directly or via a heterologous peptide or polypeptide, and in this case, the physiologically active component may be more tightly adhered to a scaffold fiber, and detachment of the physiologically active component during cell culture may be minimized.

In addition, as the physiologically active component, a known mussel protein or a specific domain or motif of a mussel protein may be included to improve cell adhesion. The domain or motif may serve to fix cells to be cultured on a cell scaffold in an early stage to prevent suspension of the cells in a culture medium, and/or to fix the physiologically active component to a scaffold fiber to prevent detachment of the physiologically active component during cell culture on a scaffold fiber. The adhesive component may be any known adhesive component that does not exhibit cytotoxicity in terms of conventional biocompatibility without limitation, and preferably includes one or more types selected from the group consisting of proteins comprising 1 to 20 repeats of amino acids of SEQ ID NOs: 1 to 7 and proteins produced by fusing at least two thereof, and therefore there are advantages in which cytotoxicity is considerably decreased, the physiologically active component has excellent adhesive strength, and detachment of the physiologically active component and isolation of cells, which occur by dissolving the adhesive component in a culture medium during cell culture, are prevented. The physiologically active component may be fixed on a fiber surface, for example, by a coating process. In addition, the physiologically active component may be mixed with the fiber-forming component in a spinning solution for producing a fiber from a fiber producing step. In this case, there is an advantage of easy inclusion of the physiologically active component on the outer surface of a produced fiber without a separate coating process or adhesive component.

In addition, combination yarn for a cell culture scaffold may be implemented with a plurality of the above-described yarns for a cell culture scaffold according to an exemplary embodiment of the present invention.

Figure 5:
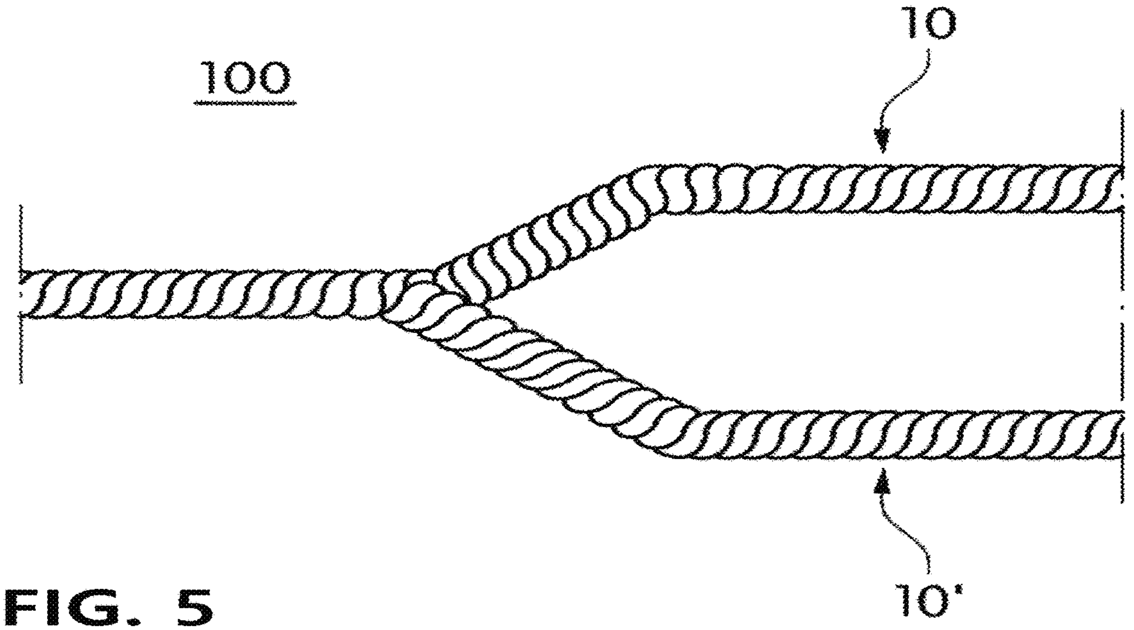
FIG. 5 is an exploded perspective view of ply yarn according to an exemplary embodiment of the present invention.

In addition, as shown in FIG. 5, ply yarn 100 for a cell culture scaffold, which includes a plurality of the yarns for a cell culture scaffold 10 and 10' according to an exemplary embodiment of the present invention, a plurality of macrotwists formed by twisting the yarns, and macrofiber grooves which are spaces between the macrotwists for providing three-dimensional growth spaces and migration paths for cells, may be implemented. Due to the macrofiber grooves formed by an outer surface curvature of the plurality of yarns and the fiber grooves included in each yarn, the ply yarn is more advantageous for the three-dimensional growth of cells, and provides the migration path of cells such that the cells can be proliferated in a uniform shape and differentiate uniformly. Meanwhile, when the yarn includes multiple fiber strands, the microfiber groove between fibers further provides the growth space and migration path of cells, and a desired cell cluster may be more easily cultured.

The ply yarn may have a fineness of 0.5 to 1000 deniers, a twist number of 100 to 5000 T/m and a twist angle of 20 to 60°, and thus it may be more suitable for attaining the object of the present invention, such that the cells are grown in a more uniform shape and more advantageous for three-dimensional growth of cells.

Meanwhile, the present invention may provide a fabric for cell culture using the yarn according to the present invention, the combination yarn thereof or the ply yarn produced by twisting the same.

The fabric may be any one of a woven fabric, a knitted fabric and a non-woven fabric, and the type of the fabric may vary depending on purpose. The woven fabric, knitted fabric and non-woven fabric may be produced by known corresponding methods. For example, the woven fabric may be a twill fabric produced by diagonally weaving any one or more of the above-described yarn, combination yarn and/or ply yarn as any one or more of a warp and weft. In addition, the knitted fabric may be a flat knit fabric weft-knitted by putting the above-described yarn, combination yarn and/or ply yarn into a flat knitting machine. In addition, the non-woven fabric may be produced by adding an adhesive component to short-cut yarn formed by cutting the yarn, combination yarn and/or ply yarn to a predetermined fiber length and applying heat/pressure thereto.

In addition, the present invention may provide a graft for tissue engineering, which includes cells cultured by grafting cells to be cultured into the above-described fabric. Here, the cells to be cultured may be cultured along the fiber grooves of the yarn. In addition, the cells may also be cultured simultaneously along the macrofiber grooves of the ply yarn and the fiber grooves of the yarn.

When a material of the fabric is a fiber-forming component harmless to a human body, a scaffold to which the cultured cells are adhered can be directly grafted to a human body such that the cultured cells can be engrafted into tissue more easily and stably. In addition, the cells may include one or more types of cells among any one or more stem cells selected from the group consisting of totipotent stem cells, pluripotent stem cells, multipotent stem cells, oligopotent stem cells and single stem cells, and differentiated cells selected from the group consisting of hematopoietic stem cells, liver cells, fiber cells, epithelial cells, mesothelial cells, endothelial cells, muscle cells, nerve cells, immune cells, adipose cells, cartilage cells, bone cells, blood cells and skin cells. For example, the cells may be cells having a shape which is elongated in one direction, rather than a spherical shape, or cells having a high migration property.

EXAMPLES

The present invention will be described in further detail with reference to the following examples, which however do not limit the scope of the present invention and should be construed as helping in understanding the present invention.

Example 1

Figure 6A:
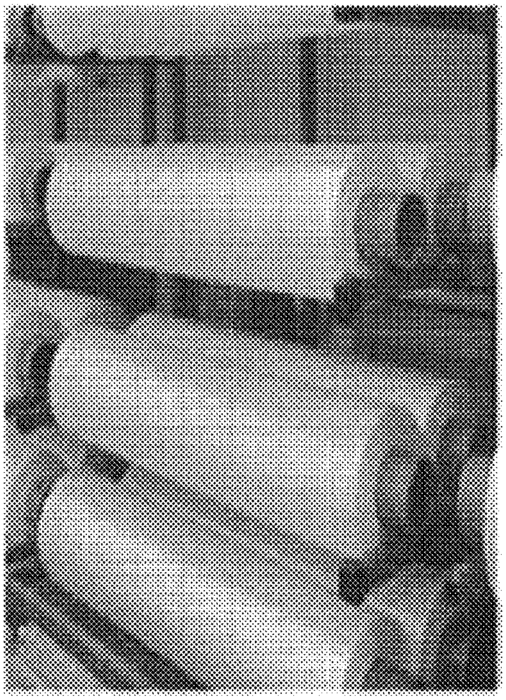
FIGS. 6A-B show an image of a 1.7M wide nanofiber web for producing slitting yarn included in an exemplary embodiment of the present invention FIG. 6A and a scanning electron microscope image of the nanofiber web FIG. 6B.
Figure 6B:
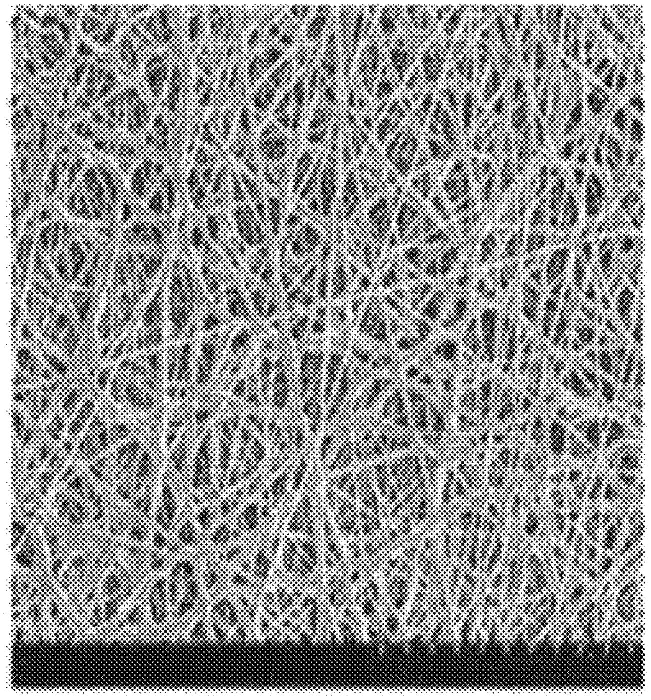

A spinning solution was prepared by dissolving PVDF as a fiber-forming component in DMAc/Acetone as a mixed solvent to have a concentration of 15 wt %. Electrospinning was performed using the prepared spinning solution and an electrospinning device under conditions of an applied voltage of 25 kV, a distance between a current collector and a spinning nozzle of 25 cm and a discharge amount of 0.05 ml/hole in an R.H. 65% environment at 30° C., thereby obtaining a roll of a nanofiber web having a width of 1.5 m, a basis weight of 5 g/m$^2$ and a length of 500 m. FIG. 6A is an image of a wound nanofiber web, and FIG. 6B is a scanning electron microscope image of the nanofiber web. As shown in FIG. 6B, an average diameter of a nanofiber forming the nanofiber web was approximately 230 nm.

Example 2

Production and Twisting of Slitting Yarn

Figure 7A:
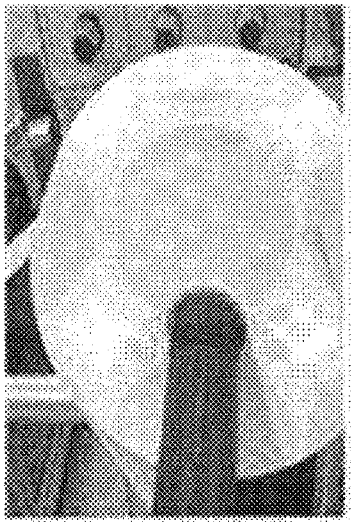
Figure 7B:
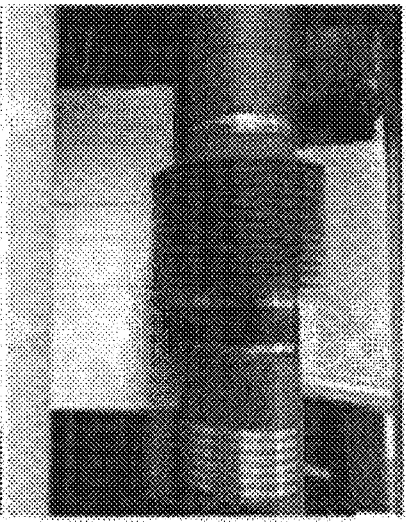
Figure 7C:
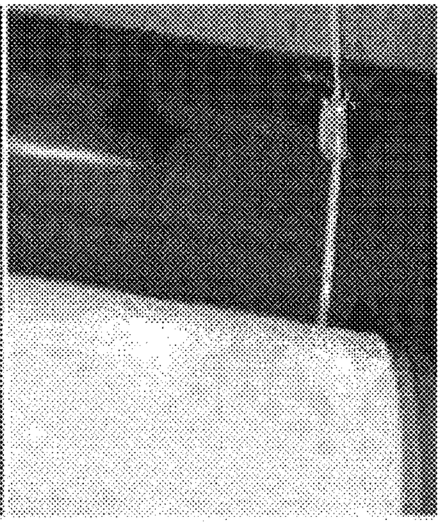
Figure 8A:
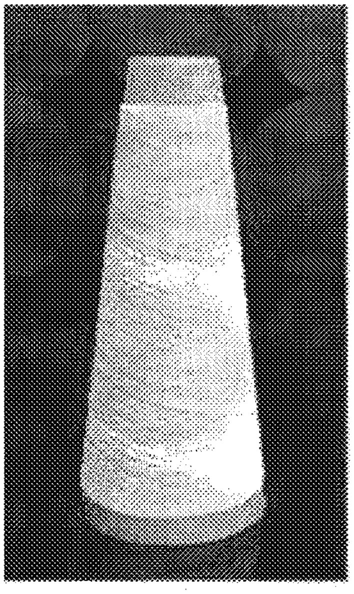
FIGS. 8A-B show an image of a cone wound with slitting yarns after braiding and twisting (FIG. 8A), and an electron microscope image of the twisted slitting yarns (FIG. 8B).
Figure 8B:
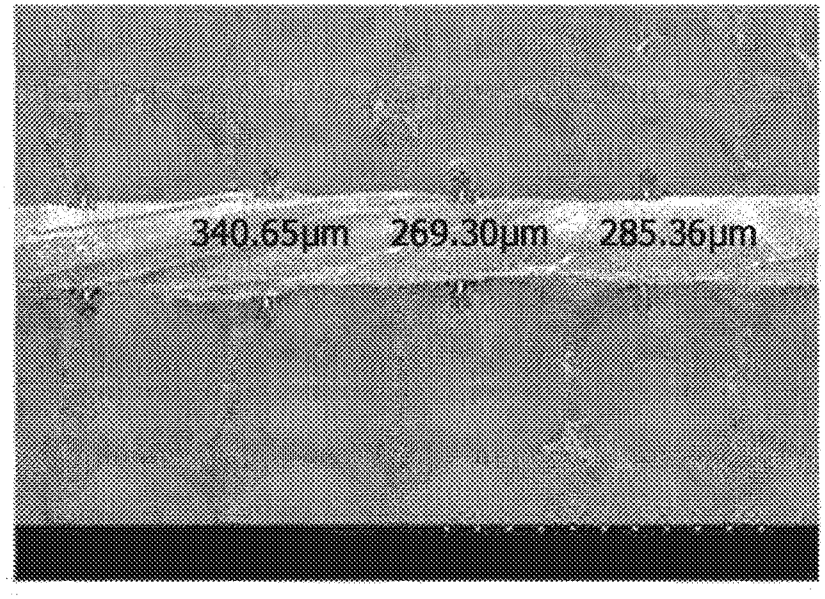

Slitting yarn was obtained by subjecting a roll of the nanofiber web produced in Example 1 to first slitting to a width of 5 mm as shown in FIG. 7A, and second precision slitting to a width of 1.5 mm as shown in FIG. 7B, and wrapping of the slitting yarn produced by the second precision slitting is shown in FIG. 7C. The produced slitting yarn had a width of 1.5 mm as shown in FIG. 3A. Yarn for a cell culture scaffold was produced by Z-twisting the slitting yarn to have a twist number of 700 T/m per minute using a 2-for-1 twisting machine. FIG. 8A shows that the twisted yarn is wrapped, and FIG. 8B is a scanning electron microscope image of the surface of the twisted yarn, showing that two strands of slitting yarns are twisted to form a plurality of twists.

Examples 3 to 5

Production of Ply Yarn

Figures 9A, 9B, 9C:
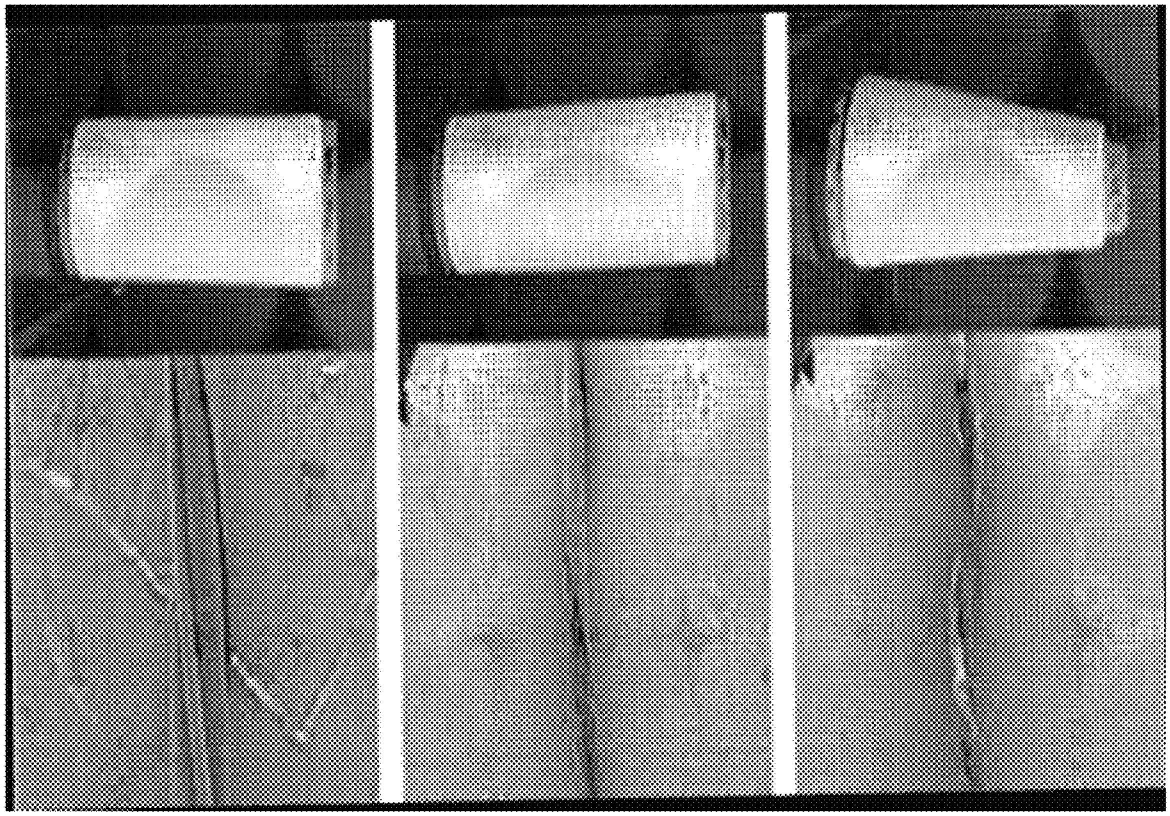
FIGS. 9A-C show a set of images according to various examples for yarns produced by combination false twisting of slitting yarn according to an exemplary embodiment of the present invention with different types of fibers, which includes FIG. 9A an electron microscope image of Example 3 produced by combination false twisting of nylon and a nanofiber, FIG. 9B an electron microscope image of Example 4 produced by combination false twisting of a polyester fiber and a nanofiber, and FIG. 9C an electron microscope image of Example 5 produced by combination false twisting of cotton and a nanofiber.

Combination false twisting was performed by braiding each of different types of yarns, such as fiber yarn of 20-denier nylon, 30-denier polyester DTY and 60-ply cotton yarn with the slitting yarn produced in Example 2 under a condition of 1000 T/m using a combination false twisting machine. FIGS. 9A-9C show an image and a scanning electron microscope image of the produced combination false twisted yarn. As shown in FIGS. 9A-9C, even when ply yarn is produced with slitting yarn and a different type of yarn, it can be confirmed that the ply yarn is actively produced without trimming, and a plurality of twists are formed through the ply yarn.

Experimental Example

Figure 10A:
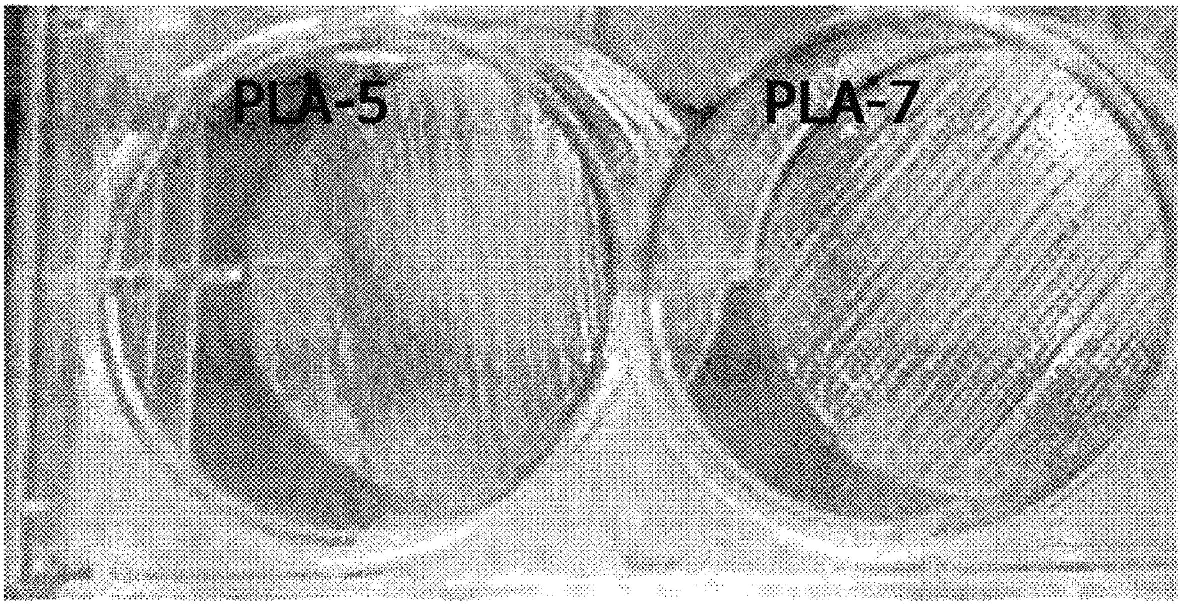
FIGS. 10A to 10D show a set of images and results of cell culture using yarn according to Example 4.

A plurality of the ply yarns produced in Example 4 were arranged parallel and fixed on a well plate for cell culture as shown in FIG. 10A. Fibroblasts (HS27) were loaded into the ply yarn-containing well plate, and then cultured in a 10% complete medium at 37° C. for 2 days. Here, the 10% complete medium was prepared by mixing Ham's F12 medium with Dulbecco's Modified Eagle Medium (DMEM) at a volume ratio of 1:1.5, and adding 7 vol % of fetal bovine serum, 65 U/mL of penicillin and 65 μg/mL of streptomycin. Afterward, DAPI staining was performed on the proliferated fibroblasts, and visualized by confocal microscopy. The results are shown in FIGS. 10B to 10D.

Figure 10B:
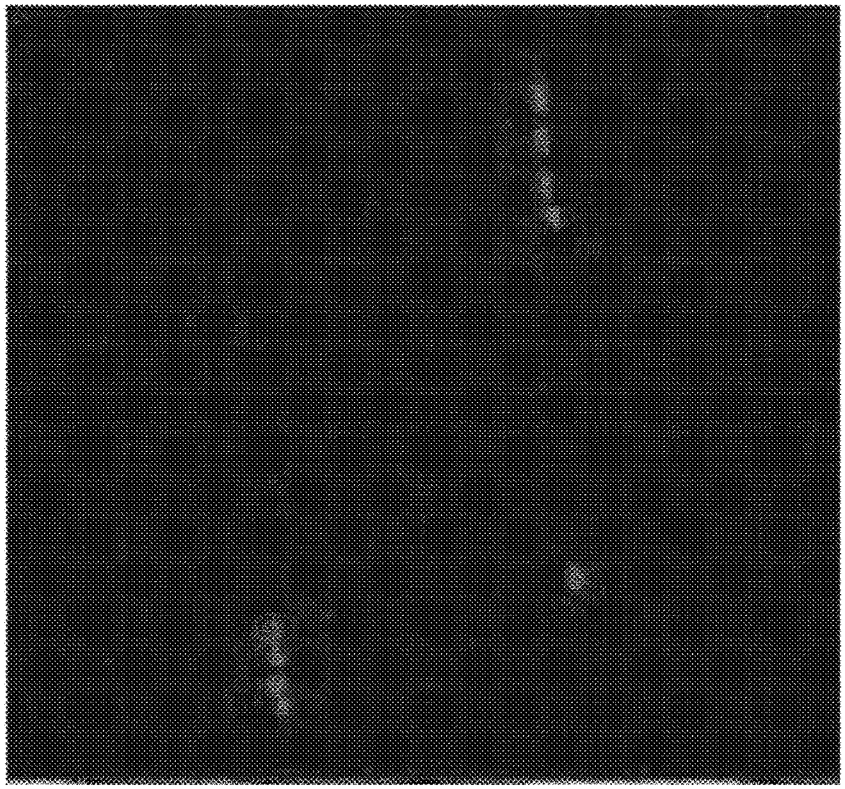
Figure 10C:
Figure 10D:
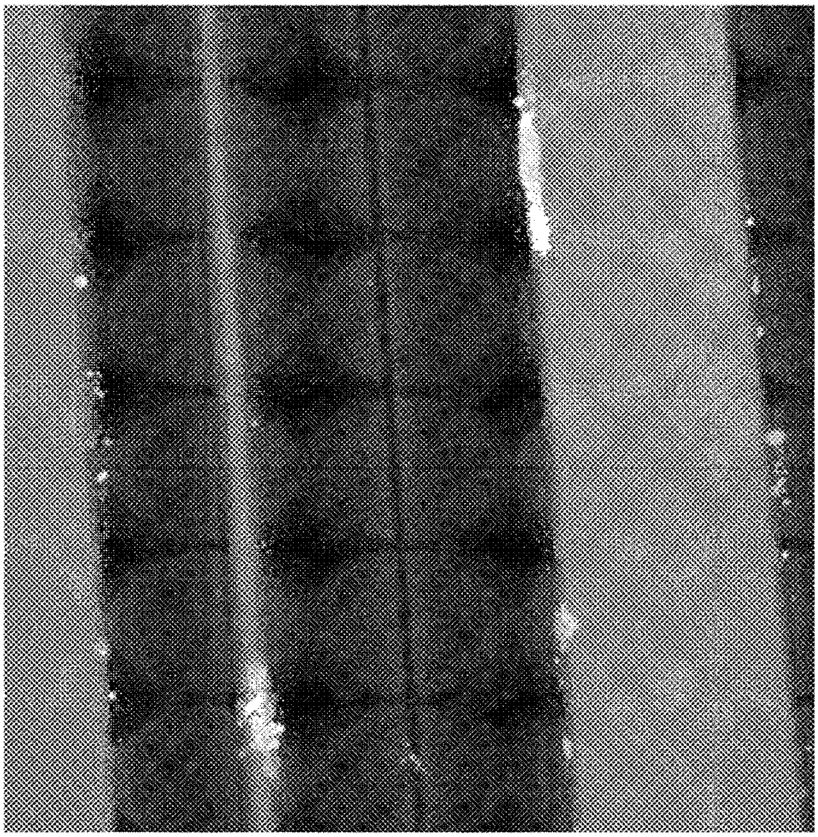

FIG. 10B shows the stained nuclei of cells, and FIG. 10C shows stained proteins in the cells. In addition, FIG. 10D shows that cells are settled in microfiber grooves between fibers and proliferated along the fiber grooves in an elongated shape.

The amino acid sequences listed under the sequence numbers described in the present invention are shown in Table 1 below.

TABLE 1

| SEQ. ID. NO: | Amino acid sequence |
|---|---|
| 1 | Met Ala Lys Pro Ser Tyr Pro Pro Thr Tyr Lys Ala Lys Pro Ser TyrPro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ser Ser Glu Glu Tyr Lys Gly Gly Tyr Tyr Pro Gly Asn Thr Tyr His Tyr His Ser Gly Gly Ser Tyr His Gly Ser Gly Tyr His Gly Gly Tyr Lys Gly Lys Tyr Tyr Gly Lys Ala Lys Lys Tyr Tyr Tyr Lys Tyr Lys Asn Ser Gly Lys Tyr Lys Tyr Leu Lys Lys Ala Arg Lys Tyr His Arg Lys Gly Tyr Lys Lys Tyr Tyr Gly Gly Ser Ser Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys |
| 2 | Met Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro |

TABLE 1-continued

| SEQ. ID. NO: | Amino acid sequence |
|---|---|
| | Pro Thr Tyr Lys Ala Lys Pro Ser Tyr Pro Pro Thr Tyr Lys Ser Ser Glu Glu Tyr Lys Gly Gly Tyr Tyr Pro Gly Asn Thr Tyr His Tyr His Ser Gly Gly Ser Tyr His Gly Ser Gly Tyr His Gly Gly Tyr Lys Gly Lys Tyr Tyr Gly Lys Ala Lys Lys Tyr Tyr Tyr Lys Tyr Lys Asn Ser Gly Lys Tyr Lys Tyr Leu Lys Lys Ala Arg Lys Tyr His Arg Lys Gly Tyr Lys Lys Tyr Tyr Gly Gly Ser Ser Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Gly Arg Gly Asp Ser Pro |
| 3 | Met Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Pro Trp Ala Asp Tyr Tyr Gly Pro Lys Tyr Gly Pro Pro Arg Arg Tyr Gly Gly Gly Asn Tyr Asn Arg Tyr Gly Arg Arg Tyr Gly Gly Tyr Lys Gly Trp Asn Asn Gly Trp Lys Arg Gly Arg Trp Gly Arg Lys Tyr Tyr Gly Ser Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Leu |
| 4 | Ala Asp Tyr Tyr Gly Pro Lys Tyr Gly Pro Pro Arg Arg Tyr Gly Gly Gly Asn Tyr Asn Arg Tyr Gly Arg Arg Tyr Gly Gly Tyr Lys Gly Trp Asn Asn Gly Trp Lys Arg Gly Arg Trp Gly Arg Lys Tyr Tyr |
| 5 | Ser Ser Glu Glu Tyr Lys Gly Gly Tyr Tyr Pro Gly Asn Thr Tyr His Tyr His Ser Gly Gly Ser Tyr His Gly Ser Gly Tyr His Gly Gly Tyr Lys Gly Lys Tyr Tyr Gly Lys Ala Lys Lys Tyr Tyr Tyr Lys Tyr Lys Asn Ser Gly Lys Tyr Lys Tyr Leu Lys Lys Ala Arg Lys Tyr His Arg Lys Gly Tyr Lys Lys Tyr Tyr Gly Gly Gly Ser Ser |
| 6 | Ala Lys Pro Ser Tyr Pro Pro Thr Tyr Lys |
| 7 | Ala Lys Pro Ser Tyr Pro Pro Thr Tyr Lys Ala Lys Pro Ser Tyr ProPro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys |
| 8 | Arg Gly Asp |
| 9 | Arg Gly Asp Ser |
| 10 | Arg Gly Asp Cys |
| 11 | Arg Gly Asp Val |
| 12 | Arg Gly Asp Ser Pro Ala Ser Ser Lys Pro |
| 13 | Gly Arg Gly Asp Ser |
| 14 | Gly Arg Gly Asp Thr Pro |
| 15 | Gly Arg Gly Asp Ser Pro |
| 16 | Gly Arg Gly Asp Ser Pro Cys |
| 17 | Tyr Arg Gly Asp Ser |
| 18 | Ser Pro Pro Arg Arg Ala Arg Val Thr |
| 19 | Trp Gln Pro Pro Arg Ala Arg Ile |
| 20 | Asn Arg Trp His Ser Ile Tyr Ile Thr Arg Phe Gly |
| 21 | Arg Lys Arg Leu Gln Val Gln Leu Ser Ile Arg Thr |
| 22 | Lys Ala Phe Asp Ile Thr Tyr Val Arg Leu Lys Phe |
| 23 | Ile Lys Val Ala Asn |
| 24 | Lys Lys Gln Arg Phe Arg His Arg Asn Arg Lys Gly Tyr Arg Ser Gln |
| 25 | Val Ala Glu Ile Asp Gly Ile Gly Leu |
| 26 | Pro His Ser Arg Asn Arg Gly Asp Ser Pro |

TABLE 1-continued

| SEQ. ID. NO: | Amino acid sequence |
|---|---|
| 27 | Asn Arg Trp His Ser Ile Tyr Ile Thr Arg Phe Gly |
| 28 | Thr Trp Tyr Lys Ile Ala Phe Gln Arg Asn Arg Lys |

Embodiments of the present invention have been described above, but the spirit of the present invention is not limited to the embodiments presented herein, and it will be understood by those of ordinary skill in the art that other embodiments may be easily suggested by adding, changing, deleting or adding components within the scope of the same idea and they are also included in the scope of the spirit of the present invention.

The invention claimed is:

1. A ply yarn for a cell culture scaffold, comprising:

a slitting yarn with a plurality of twists and fiber grooves, wherein the slitting yarn has a fineness of 0.01 to 30 denier and is a nanofiber web having a basis weight of 0.1 to 20 g/m$^2$ in a three-dimensional network structure cut into multiple strands to have a width of 0.1 to 30 mm; and the fiber grooves which are spaces formed between the twists and configured to provide three-dimensional growth spaces and migration paths for cell, wherein the ply yarn comprises a plurality of macrotwists at a twist number of 100 to 5,000 twists/meter (T/m) and a twist angle of 20° to 60°, and macrofiber grooves between the plurality of macrotwists, wherein the ply yarn has a fineness of 0.5 to 1,000 denier and the macrofiber grooves are configured to provide three-dimensional growth spaces and migration paths for cells, wherein the fiber grooves are formed continuously in the longitudinal direction of the ply yarn for a cell culture scaffold, and wherein the ply yarn for a cell culture scaffold comprises microfiber grooves, which are spaces between the slitting yarn strands, formed on an outer surface of the ply yarn.

2. The ply yarn according to claim 1, wherein the slitting yarn includes, as a fiber-forming component, any one or more non-biodegradable components selected from the group consisting of polystyrene (PS), polyethylene terephthalate (PET), polyethersulfone (PES), polyvinylidene fluoride (PVDF), polyacrylonitrile (PAN), polydimethylsiloxane (PDMS), a polyamide, a polyalkylene, a poly (alkylene oxide), a poly (amino acid), a poly (allylamine), polyphosphazene and a polyethyleneoxide-polypropyleneoxide block copolymer, or any one or more biodegradable components selected from the group consisting of polycaprolactone, polydioxanone, polyglycolic acid, poly (L-lactide) (PLLA), poly (DL-lactide-co-glycolide) (PLGA), polylactic acid and polyvinyl alcohol.

3. The ply yarn according to claim 1, wherein the slitting yarn further includes a physiologically active component which induces any one or more of adhesion, migration, growth, proliferation and differentiation of cells on an outer surface of the slitting yarn.

4. The ply yarn according to claim 3, wherein the physiologically active component includes any one or more among any one or more compounds selected from the group consisting of a monoamine, an amino acid, a peptide, a saccharide, a lipid, a protein, a glucoprotein, a glucolipid, a proteoglycan, a mucopolysaccharide and a nucleic acid, and a cell.

5. A fabric for a cell culture scaffold, comprising the ply yarn according to claim 1.

6. A method of forming a cell culture scaffold, comprising culturing one or more types of stem cells selected from the group consisting of totipotent stem cells, pluripotent stem cells, multipotent stem cells, oligopotent stem cells and single stem cells, and one or more types of differentiated cells selected from the group consisting of hematopoietic stem cells, liver cells, fiber cells, epithelial cells, mesothelial cells, endothelial cells, muscle cells, nerve cells, immune cells, adipose cells, cartilage cells, bone cells, blood cells and skin cells in the ply yarn of claim 1.

* * * * *

SEQUENCE LISTING

```
<160> NUMBER OF SEQ ID NOS: 28

<210> SEQ ID NO 1
<211> LENGTH: 196
<212> TYPE: PRT
<213> ORGANISM: Artificial Sequence
<220> FEATURE:
<223> OTHER INFORMATION: Motif for cell culture scaffold

<400> SEQUENCE: 1

Met Ala Lys Pro Ser Tyr Pro Pro Thr Tyr Lys Ala Lys Pro Ser Tyr
1               5                   10                  15

Pro Pro Thr Tyr Lys Ala Lys Pro Ser Tyr Pro Pro Thr Tyr Lys Ala
            20                  25                  30

Lys Pro Ser Tyr Pro Pro Thr Tyr Lys Ala Lys Pro Ser Tyr Pro Pro
        35                  40                  45

Thr Tyr Lys Ala Lys Pro Ser Tyr Pro Pro Thr Tyr Lys Ser Ser Glu
    50                  55                  60

Glu Tyr Lys Gly Gly Tyr Tyr Pro Gly Asn Thr Tyr His Tyr His Ser
65                  70                  75                  80

Gly Gly Ser Tyr His Gly Ser Gly Tyr His Gly Gly Tyr Lys Gly Lys
                85                  90                  95

Tyr Tyr Gly Lys Ala Lys Lys Tyr Tyr Tyr Lys Tyr Lys Asn Ser Gly
            100                 105                 110

Lys Tyr Lys Tyr Leu Lys Lys Ala Arg Lys Tyr His Arg Lys Gly Tyr
        115                 120                 125

Lys Lys Tyr Tyr Gly Gly Ser Ser Ala Lys Pro Ser Tyr Pro Pro Thr
    130                 135                 140

Tyr Lys Ala Lys Pro Ser Tyr Pro Pro Thr Tyr Lys Ala Lys Pro Ser
145                 150                 155                 160

Tyr Pro Pro Thr Tyr Lys Ala Lys Pro Ser Tyr Pro Pro Thr Tyr Lys
                165                 170                 175

Ala Lys Pro Ser Tyr Pro Pro Thr Tyr Lys Ala Lys Pro Ser Tyr Pro
            180                 185                 190

Pro Thr Tyr Lys
        195


<210> SEQ ID NO 2
<211> LENGTH: 202
<212> TYPE: PRT
<213> ORGANISM: Artificial Sequence
<220> FEATURE:
<223> OTHER INFORMATION: Motif for cell culture scaffold
```

<400> SEQUENCE: 2

Met Ala Lys Pro Ser Tyr Pro Pro Thr Tyr Lys Ala Lys Pro Ser Tyr
1 5 10 15

Pro Pro Thr Tyr Lys Ala Lys Pro Ser Tyr Pro Pro Thr Tyr Lys Ala
20 25 30

Lys Pro Ser Tyr Pro Pro Thr Tyr Lys Ala Lys Pro Ser Tyr Pro Pro
35 40 45

Thr Tyr Lys Ala Lys Pro Ser Tyr Pro Pro Thr Tyr Lys Ser Ser Glu
50 55 60

Glu Tyr Lys Gly Gly Tyr Tyr Pro Gly Asn Thr Tyr His Tyr His Ser
65 70 75 80

Gly Gly Ser Tyr His Gly Ser Gly Tyr His Gly Gly Tyr Lys Gly Lys
85 90 95

Tyr Tyr Gly Lys Ala Lys Lys Tyr Tyr Tyr Lys Tyr Lys Asn Ser Gly
100 105 110

Lys Tyr Lys Tyr Leu Lys Lys Ala Arg Lys Tyr His Arg Lys Gly Tyr
115 120 125

Lys Lys Tyr Tyr Gly Gly Ser Ser Ala Lys Pro Ser Tyr Pro Pro Thr
130 135 140

Tyr Lys Ala Lys Pro Ser Tyr Pro Pro Thr Tyr Lys Ala Lys Pro Ser
145 150 155 160

Tyr Pro Pro Thr Tyr Lys Ala Lys Pro Ser Tyr Pro Pro Thr Tyr Lys
165 170 175

Ala Lys Pro Ser Tyr Pro Pro Thr Tyr Lys Ala Lys Pro Ser Tyr Pro
180 185 190

Pro Thr Tyr Lys Gly Arg Gly Asp Ser Pro
195 200

<210> SEQ ID NO 3
<211> LENGTH: 172
<212> TYPE: PRT
<213> ORGANISM: Artificial Sequence
<220> FEATURE:
<223> OTHER INFORMATION: Motif for cell culture scaffold

<400> SEQUENCE: 3

Met Ala Lys Pro Ser Tyr Pro Pro Thr Tyr Lys Ala Lys Pro Ser Tyr
1 5 10 15

Pro Pro Thr Tyr Lys Ala Lys Pro Ser Tyr Pro Pro Thr Tyr Lys Ala
20 25 30

Lys Pro Ser Tyr Pro Pro Thr Tyr Lys Ala Lys Pro Ser Tyr Pro Pro
35 40 45

Thr Tyr Lys Ala Lys Pro Ser Tyr Pro Pro Thr Tyr Lys Pro Trp Ala
50 55 60

Asp Tyr Tyr Gly Pro Lys Tyr Gly Pro Pro Arg Arg Tyr Gly Gly Gly
65 70 75 80

Asn Tyr Asn Arg Tyr Gly Arg Arg Tyr Gly Gly Tyr Lys Gly Trp Asn
85 90 95

Asn Gly Trp Lys Arg Gly Arg Trp Gly Arg Lys Tyr Tyr Gly Ser Ala
100 105 110

Lys Pro Ser Tyr Pro Pro Thr Tyr Lys Ala Lys Pro Ser Tyr Pro Pro
115 120 125

Thr Tyr Lys Ala Lys Pro Ser Tyr Pro Pro Thr Tyr Lys Ala Lys Pro
130 135 140

-continued

```
Ser Tyr Pro Pro Thr Tyr Lys Ala Lys Pro Ser Tyr Pro Pro Thr Tyr
145                 150                 155                 160

Lys Ala Lys Pro Ser Tyr Pro Pro Thr Tyr Lys Leu
                165                 170


<210> SEQ ID NO 4
<211> LENGTH: 46
<212> TYPE: PRT
<213> ORGANISM: Artificial Sequence
<220> FEATURE:
<223> OTHER INFORMATION: Motif for cell culture scaffold

<400> SEQUENCE: 4

Ala Asp Tyr Tyr Gly Pro Lys Tyr Gly Pro Pro Arg Arg Tyr Gly Gly
1               5                   10                  15

Gly Asn Tyr Asn Arg Tyr Gly Arg Arg Tyr Gly Gly Tyr Lys Gly Trp
            20                  25                  30

Asn Asn Gly Trp Lys Arg Gly Arg Trp Gly Arg Lys Tyr Tyr
        35                  40                  45


<210> SEQ ID NO 5
<211> LENGTH: 76
<212> TYPE: PRT
<213> ORGANISM: Artificial Sequence
<220> FEATURE:
<223> OTHER INFORMATION: Motif for cell culture scaffold

<400> SEQUENCE: 5

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser
65                  70                  75


<210> SEQ ID NO 6
<211> LENGTH: 10
<212> TYPE: PRT
<213> ORGANISM: Artificial Sequence
<220> FEATURE:
<223> OTHER INFORMATION: Motif for cell culture scaffold

<400> SEQUENCE: 6

Ala Lys Pro Ser Tyr Pro Pro Thr Tyr Lys
1               5                   10


<210> SEQ ID NO 7
<211> LENGTH: 60
<212> TYPE: PRT
<213> ORGANISM: Artificial Sequence
<220> FEATURE:
<223> OTHER INFORMATION: Motif for cell culture scaffold

<400> SEQUENCE: 7

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30
```

-continued

Pro Ser Tyr Pro Pro Thr Tyr Lys Ala Lys Pro Ser Tyr Pro Pro Thr
35 40 45

Tyr Lys Ala Lys Pro Ser Tyr Pro Pro Thr Tyr Lys
50 55 60

<210> SEQ ID NO 8
<211> LENGTH: 3
<212> TYPE: PRT
<213> ORGANISM: Artificial Sequence
<220> FEATURE:
<223> OTHER INFORMATION: Motif for cell culture scaffold

<400> SEQUENCE: 8

Arg Gly Asp
1

<210> SEQ ID NO 9
<211> LENGTH: 4
<212> TYPE: PRT
<213> ORGANISM: Artificial Sequence
<220> FEATURE:
<223> OTHER INFORMATION: Motif for cell culture scaffold

<400> SEQUENCE: 9

Arg Gly Asp Ser
1

<210> SEQ ID NO 10
<211> LENGTH: 4
<212> TYPE: PRT
<213> ORGANISM: Artificial Sequence
<220> FEATURE:
<223> OTHER INFORMATION: Motif for cell culture scaffold

<400> SEQUENCE: 10

Arg Gly Asp Cys
1

<210> SEQ ID NO 11
<211> LENGTH: 4
<212> TYPE: PRT
<213> ORGANISM: Artificial Sequence
<220> FEATURE:
<223> OTHER INFORMATION: Motif for cell culture scaffold

<400> SEQUENCE: 11

Arg Gly Asp Val
1

<210> SEQ ID NO 12
<211> LENGTH: 10
<212> TYPE: PRT
<213> ORGANISM: Artificial Sequence
<220> FEATURE:
<223> OTHER INFORMATION: Motif for cell culture scaffold

<400> SEQUENCE: 12

Arg Gly Asp Ser Pro Ala Ser Ser Lys Pro
1 5 10

<210> SEQ ID NO 13
<211> LENGTH: 5
<212> TYPE: PRT
<213> ORGANISM: Artificial Sequence
<220> FEATURE:
<223> OTHER INFORMATION: Motif for cell culture scaffold -continued

<400> SEQUENCE: 13

Gly Arg Gly Asp Ser
1               5

<210> SEQ ID NO 14
<211> LENGTH: 6
<212> TYPE: PRT
<213> ORGANISM: Artificial Sequence
<220> FEATURE:
<223> OTHER INFORMATION: Motif for cell culture scaffold

<400> SEQUENCE: 14

Gly Arg Gly Asp Thr Pro
1               5

<210> SEQ ID NO 15
<211> LENGTH: 6
<212> TYPE: PRT
<213> ORGANISM: Artificial Sequence
<220> FEATURE:
<223> OTHER INFORMATION: Motif for cell culture scaffold

<400> SEQUENCE: 15

Gly Arg Gly Asp Ser Pro
1               5

<210> SEQ ID NO 16
<211> LENGTH: 7
<212> TYPE: PRT
<213> ORGANISM: Artificial Sequence
<220> FEATURE:
<223> OTHER INFORMATION: Motif for cell culture scaffold

<400> SEQUENCE: 16

Gly Arg Gly Asp Ser Pro Cys
1               5

<210> SEQ ID NO 17
<211> LENGTH: 5
<212> TYPE: PRT
<213> ORGANISM: Artificial Sequence
<220> FEATURE:
<223> OTHER INFORMATION: Motif for cell culture scaffold

<400> SEQUENCE: 17

Tyr Arg Gly Asp Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Motif for cell culture scaffold

<400> SEQUENCE: 18

Ser Pro Pro Arg Arg Ala Arg Val Thr
1               5

<210> SEQ ID NO 19
<211> LENGTH: 8
<212> TYPE: PRT
<213> ORGANISM: Artificial Sequence
<220> FEATURE:
<223> OTHER INFORMATION: Motif for cell culture scaffold

<400> SEQUENCE: 19

Trp Gln Pro Pro Arg Ala Arg Ile
1 5

<210> SEQ ID NO 20
<211> LENGTH: 12
<212> TYPE: PRT
<213> ORGANISM: Artificial Sequence
<220> FEATURE:
<223> OTHER INFORMATION: Motif for cell culture scaffold

<400> SEQUENCE: 20

Asn Arg Trp His Ser Ile Tyr Ile Thr Arg Phe Gly
1 5 10

<210> SEQ ID NO 21
<211> LENGTH: 12
<212> TYPE: PRT
<213> ORGANISM: Artificial Sequence
<220> FEATURE:
<223> OTHER INFORMATION: Motif for cell culture scaffold

<400> SEQUENCE: 21

Arg Lys Arg Leu Gln Val Gln Leu Ser Ile Arg Thr
1 5 10

<210> SEQ ID NO 22
<211> LENGTH: 12
<212> TYPE: PRT
<213> ORGANISM: Artificial Sequence
<220> FEATURE:
<223> OTHER INFORMATION: Motif for cell culture scaffold

<400> SEQUENCE: 22

Lys Ala Phe Asp Ile Thr Tyr Val Arg Leu Lys Phe
1 5 10

<210> SEQ ID NO 23
<211> LENGTH: 5
<212> TYPE: PRT
<213> ORGANISM: Artificial Sequence
<220> FEATURE:
<223> OTHER INFORMATION: Motif for cell culture scaffold

<400> SEQUENCE: 23

Ile Lys Val Ala Asn
1 5

<210> SEQ ID NO 24
<211> LENGTH: 16
<212> TYPE: PRT
<213> ORGANISM: Artificial Sequence
<220> FEATURE:
<223> OTHER INFORMATION: Motif for cell culture scaffold

<400> SEQUENCE: 24

Lys Lys Gln Arg Phe Arg His Arg Asn Arg Lys Gly Tyr Arg Ser Gln
1 5 10 15

<210> SEQ ID NO 25
<211> LENGTH: 9
<212> TYPE: PRT
<213> ORGANISM: Artificial Sequence
<220> FEATURE:
<223> OTHER INFORMATION: Motif for cell culture scaffold -continued

```
<400> SEQUENCE: 25

Val Ala Glu Ile Asp Gly Ile Gly Leu
1               5


<210> SEQ ID NO 26
<211> LENGTH: 10
<212> TYPE: PRT
<213> ORGANISM: Artificial Sequence
<220> FEATURE:
<223> OTHER INFORMATION: Motif for cell culture scaffold

<400> SEQUENCE: 26

Pro His Ser Arg Asn Arg Gly Asp Ser Pro
1               5                   10


<210> SEQ ID NO 27
<211> LENGTH: 12
<212> TYPE: PRT
<213> ORGANISM: Artificial Sequence
<220> FEATURE:
<223> OTHER INFORMATION: Motif for cell culture scaffold

<400> SEQUENCE: 27

Asn Arg Trp His Ser Ile Tyr Ile Thr Arg Phe Gly
1               5                   10


<210> SEQ ID NO 28
<211> LENGTH: 12
<212> TYPE: PRT
<213> ORGANISM: Artificial Sequence
<220> FEATURE:
<223> OTHER INFORMATION: Motif for cell culture scaffold

<400> SEQUENCE: 28

Thr Trp Tyr Lys Ile Ala Phe Gln Arg Asn Arg Lys
1               5                   10
```